United States Patent [19]

Baldwin

[11] Patent Number: 5,510,610
[45] Date of Patent: Apr. 23, 1996

[54] APPARATUS FOR DETECTING DEFECTS ON THE BOTTOM OF BOTTLES BY MANIPULATING AN IMAGE TO REMOVE KNURLS

[75] Inventor: Leo B. Baldwin, Horseheads, N.Y.

[73] Assignee: Emhart Glass Machinery Investments Inc., Wilmington, Del.

[21] Appl. No.: 319,911

[22] Filed: Oct. 7, 1994

[51] Int. Cl.⁶ .................................................. G06M 7/00
[52] U.S. Cl. .............................. 250/223 B; 250/559.45; 250/559.46; 356/240; 209/526
[58] Field of Search ............................... 250/223 B, 572, 250/562, 559.46, 559.45; 356/239, 240; 209/522, 523, 524, 526; 348/125, 127, 128

[56] References Cited

U.S. PATENT DOCUMENTS

| | | | |
|---|---|---|---|
| 4,428,673 | 1/1984 | Yoshida | 356/240 |
| 4,900,916 | 2/1990 | Cormack | 250/223 B |
| 4,943,713 | 7/1990 | Yoshida | 250/223 B |
| 4,959,537 | 9/1990 | Kimoto et al. | 250/223 B |
| 5,095,204 | 3/1992 | Novini | 250/223 B |
| 5,349,435 | 9/1994 | Hall et al. | 356/240 |
| 5,354,984 | 10/1994 | Baldwin | 250/223 B |

*Primary Examiner*—Edward P. Westin
*Assistant Examiner*—Stephen Calogero
*Attorney, Agent, or Firm*—Spencer T. Smith

[57] ABSTRACT

An algorithm is disclosed which effectively removes the knurled annular portion on the bottom of a glass or plastic bottle which is located at an inspection location where diffused light is shown through the bottom of the bottle and is observed by a camera looking down through the bottle opening. The annular area is unwrapped and differenced to eliminate the knurling so that defects can be defined.

4 Claims, 4 Drawing Sheets

FIG. 2
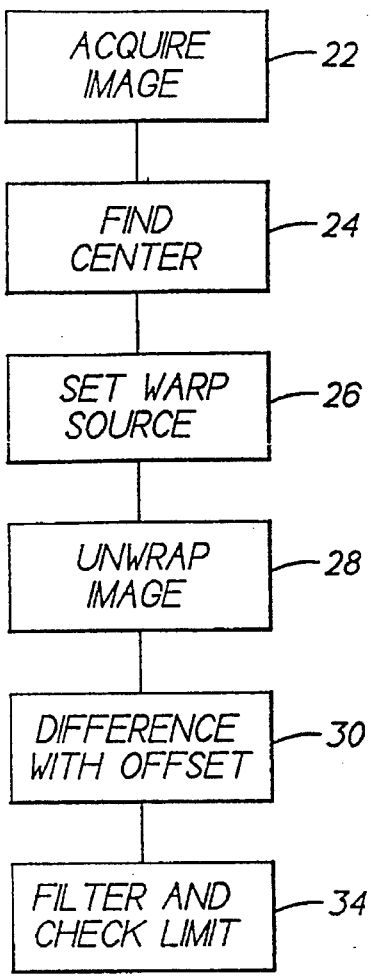
FIG. 1
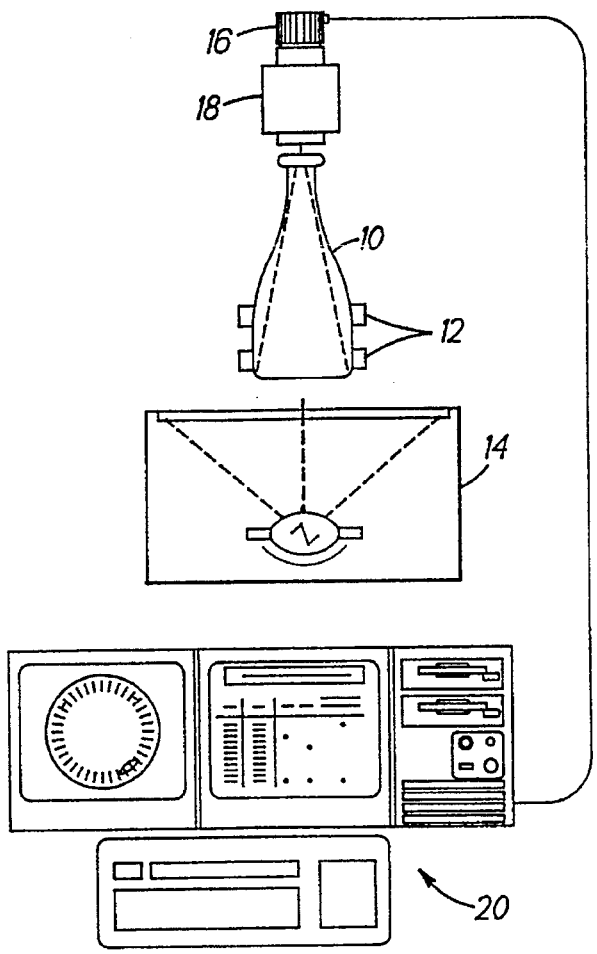
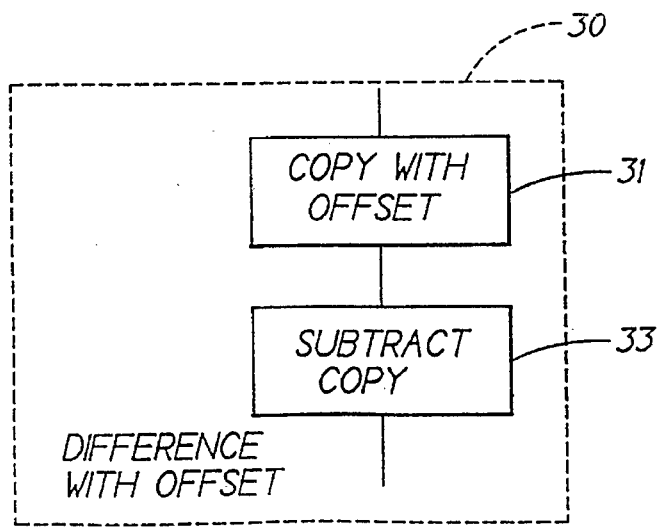
FIG. 3

1

APPARATUS FOR DETECTING DEFECTS ON THE BOTTOM OF BOTTLES BY MANIPULATING AN IMAGE TO REMOVE KNURLS

FIELD OF THE INVENTION

The present invention relates to the inspection of the knurled annular area on the bottom of a glass or plastic container.

The purpose of this invention is to evaluate the bottoms of glass and plastic containers to detect defects or contamination in the bottoms despite the presence of features which are deliberately placed there for identification, trade marking or strengthening or features which are acceptable relics of the forming process. This inspection may be performed at the place of manufacture after the bottle is produced, or at the place of filling prior to the filling operation. Examples of defects are foreign matter including air bubbles which are embedded within the bottom of the container, foreign matter which is loose within the container, and malformations in container bottom.

DESCRIPTION OF THE RELATED ART

In current devices, a handling mechanism presents the container to an inspection station. The inspection station consists of a diffuse backlight below the container directing illumination upwards and a camera with a lens above the container viewing the bottom of the container through the neck opening. The lens images the bottom of the bottle onto a sensor which converts the image into an electronic signal which in turn is analyzed electronically by dedicated electronic circuitry or a suitably programmed computing device.

The analysis typically compares the intensity of a picture element (pixel), or the average or total intensity of a small group of pixels with another pixel or like group of pixels which is displaced a predetermined distance and direction from the subject pixel. The direction and distance of the displacement from the subject pixel to the reference pixel is chosen to use any symmetries in the container bottom to advantage. For example, in the base of a round glass bottle a peripheral annular area will bear a pattern of essentially radial protrusions called knurling which are deliberately formed to inhibit radial crack propagation over the life of the bottle. In a typical inspection process the average intensity of a small region of pixels within the knurling will be compared to the average intensity of a like group of pixels also within the knurling at a fixed distance within the annular knurling region from the first group. Several such areas are compared with similarly offset reference areas until the entire knurled region has been inspected, in a process known as block processing. In other areas of the bottle, where knurling is absent, the offset between the subject pixel or group of pixels and the reference pixel or group of pixels may be radial, annular, or both in a process known as spiral processing.

It is an object of the present invention to provide an improved algorithm for identifying defects within the knurled area of the bottom of a glass or plastic container.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE DRAWINGS

Referring to the drawings:

FIG. 1 is a physical component layout of an inspection machine made in accordance with the teachings of the present invention;

FIG. 2 is a flow chart of the algorithm of the present invention;

FIG. 3 is a flow chart of one step in the algorithm shown in FIG. 2;

DESCRIPTION OF THE PREFERRED EMBODIMENT

Figure 4:
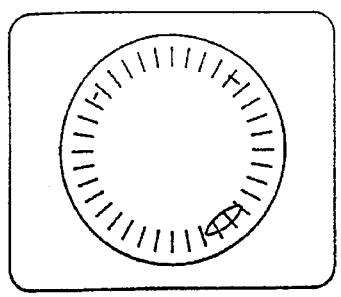
FIG. 4 is a frame showing a representation of the acquired image.

A bottle 10 is transported to the illustrated inspection station where the view of the bottom of the bottle will not be obstructed by side gripping belts 12. A diffuse backlight 14 positioned under the bottle illuminates the bottom of the bottle, and a camera 16 and lens 18 positioned above the bottle look down through the neck of the bottle to image the bottom of the bottle onto the camera sensor which is an area array electronic sensor. If narrow necked containers such as beverage bottles are to be examined a wider range of container will be accommodated if the camera lens is telocentric in image space such that the entrance pupil can be positioned immediately above the neck opening of the container. The camera signal is interfaced to a computing device which is capable of digitizing the camera signal into addressable memory and analyzing the stored image in accordance with a stored algorithm.

A description of the sequence of operations used to identify defects within the knurling is shown in FIGS. 2 and 3. In the first operation 22 (Acquire Image) an image is acquired from the electronic camera into the addressable memory space of a digital image processing device. The image as stored in the memory space is represented by the frame shown in FIG. 4. This image is of a spatial resolution sufficiently high to insure the required measurement accuracy (for instance 512 picture elements by 512 picture elements) and sufficient amplitude resolution to insure that the projected image of the bottle can be distinguished from its background (for example, if the signal from the camera is converted to digital format with 8 binary of resolution and the frame store memory can store at least 8 binary digits at each addressable location the continuum of intensity levels present in the optical image may be represented as 256 discreet levels of brightness). The electronic image may be enhanced by any of the customary digital image processing techniques such as histogram equalization, or remapping the intensity representation, for example by means of a look-up-table.

Figure 5:
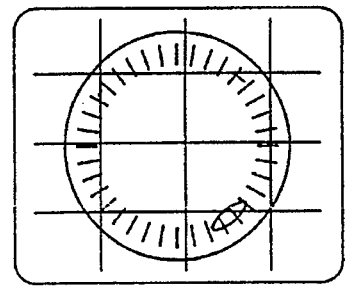
FIG. 5 is a frame showing a representation of the centered acquired image.

In the second operation 24 (Find Center), the center of the image is found, and if non-round, the orientation is also found. For example, the midpoints of intersection between a number of digitally constructed lines deployed horizontally and the bottle image perimeter may be averaged, and similarly the midpoints of intersection between vertically deployed lines and the bottle image perimeter may be averaged, with these two averages giving a coordinate pair which specifies the center of the image in terms of the number of pixels from the left side of the image and the number of picture elements ("pixels") down from the top side of the image. This method has been graphically illustrated in FIG. 5. Alternately, other methods commonly known such as using the center of a bounding box which is just large enough to frame the image may be employed.

Figure 6:
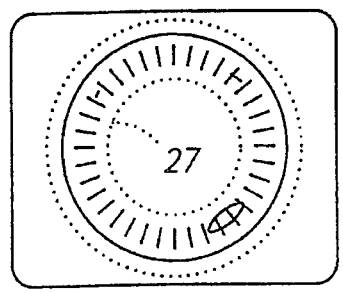
FIG. 6 is a frame showing a representation of the image and the area to be remapped (warped)

In the third operation 26 (Set Warp Source), an annular area 27 is defined (FIG. 6) which encompasses the region known as the knurling and has a geometry which follows that of the knurled area. The annular area may be circular or it may deviate from a circle in order to follow the geometry of the knurled area which may be oblong, square, rectangular or crescent shaped, for example. This section area may be based solely on preprogrammed information and expected bottle position at the time of image capture but here it is shown to be adaptive: the basic geometry of the knurled area is preprogrammed when the machine is set up to run a particular bottle but the exact orientation and location of the source area is determined separately for each case based on the information extracted in the location operation 24.

Figure 7:
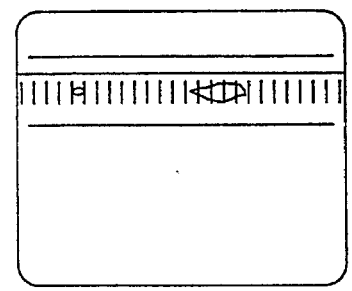
FIG. 7 is a frame showing a representation of a warped image.

In the fourth operation 28 (Unwrap Image), the annular area 27 is remapped into another digital memory space such that the knurling is laid out in one or more straight lines (FIG. 7). In general, the pixel area of the source image area will be preserved in the remapping as well as the general spatial relationships between features in the source and remapped images. This operation is known within the art as "warping" of the image, and is a discreet implementation of the geometric operation known as conformal mapping. The warping may be done with or without interpolation between adjacent pixels.

Figure 8:
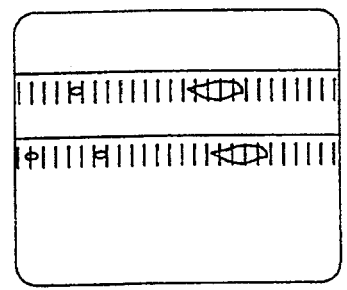
FIG. 8 is a frame showing a representation of a laterally offset image.

In the fifth operation 30 (Difference With Offset), a copy of the remapped knurled area can be made with a lateral offset 31 (Copy With Offset) equal (or as near equal as possible) to a whole number knurling pitches (FIG. 8). Note that the ratio relating pixel pitch and knurling pitch may be an irrational number and therefore an approximation to a rational number may have to be made to accommodate the offset within the spatial resolution limits of the image memory. During the offset the image is wrapped. In FIG. 8, the copy image is shifted to the right. The piece of the image which would be "off the screen" is pasted into the space on the left side. In this way, the remapped image of the knurling and its offset copy are aligned on the knurling pitch and are the same length with endpoints aligned.

Figure 9:
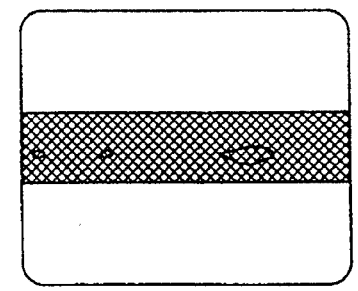
FIG. 9 is a frame showing a representation of an offset image subtracted from the original image.

The offset copy of the remapped image is subtracted 33 (Subtract Copy) from the remapped image (FIG. 9). Since the offset is aligned by a whole number of periods of the periodic structure of the knurling, the knurling will in general disappear. Defects, however, will not be aligned between the remapped image and its offset copy and will hence not cancel out: in fact, they will be twinned. The defect in the remapped image will not be aligned with its counterpart in the offset copy, and hence will not be negated. The defect in the offset copy will not be aligned with its counterpart in the remapped image and in the subtraction operation (FIG. 9) will result in a negative image of the defect, offset from the amount of the offset between the remapped image and its offset copy. Optionally, where the knurled area is circular or otherwise symmetrical, the annular knurled area can be remapped to define a difference image in which the knurling image disappears by rotating a copy of the annular image relative to the original image, by an amount that allows the knurling patterns to line up.

Figure 10:
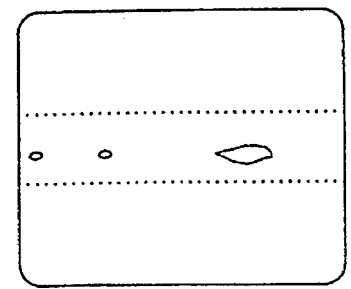
FIG. 10 is a frame showing a representation of the filtered subtracted image.

It does not matter for the algorithm that the difference image may contain negative intensities. This may, however, pose a problem in the display of the difference image. This can be handled several ways, for instance, the negative number may be remapped as positive intensities in a different color plane if one is available. In FIG. 10 the difference image has been remapped onto a gray scale image such that zero maps to the median intensity, the minimum negative intensity maps to zero, and the positive intensities are compressed in the mapping from zero to maximum values onto median to maximum values. The negative values are similarly compressed in their mapping from zero to minimum values onto median to zero intensities.

Optionally, in the fifth operation 30 (Difference With Offset), the image or array can be differenced by a procedure whereby the minuend pixel or array element and the subtrahend pixel or array element are individually referenced from the same source and differenced. The result may be placed in a newly created image or array or result may replace the minuend or subtrahend, whichever one will not be referenced again, to difference the array "in place." This method may provide an advantage in speed or memory requirements in certain processing architectures.

Figure 11:
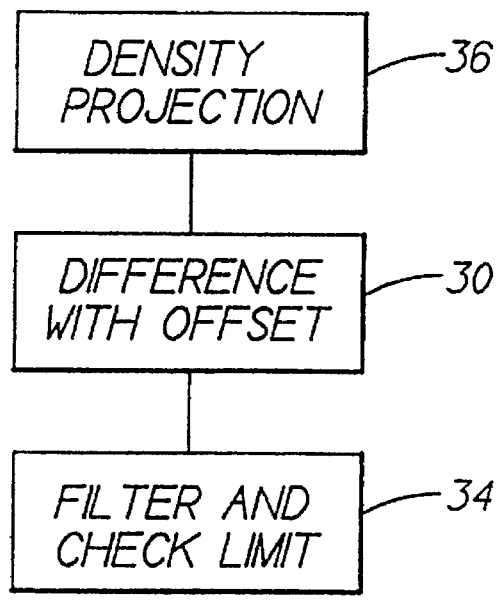
FIG. 11 is a flow chart showing of a first variation in the disclosed algorithm.
Figure 15:
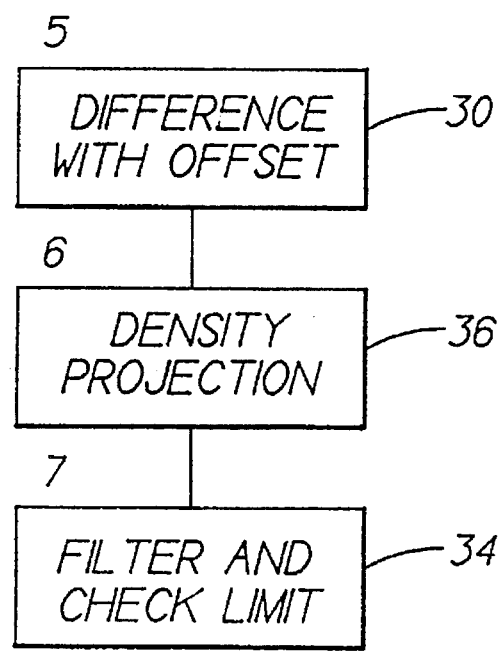
FIG. 15 is a flow chart of a second variation in the disclosed algorithm.
Figure 12:
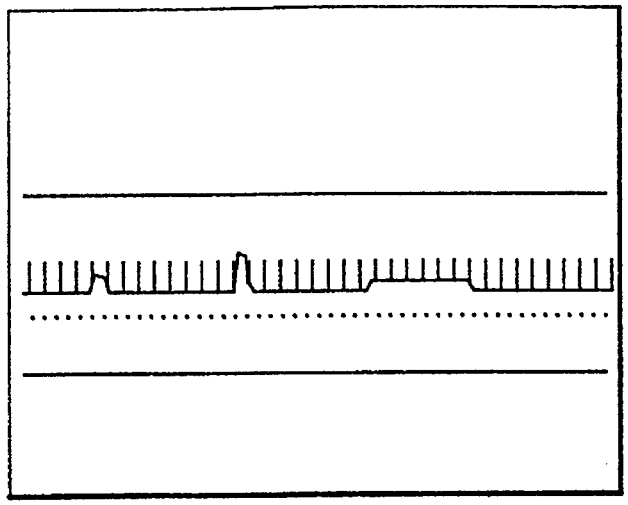
FIG. 12 is a frame showing a vertical projected array of the unwrapped image following the step of density projection.
Figure 13:
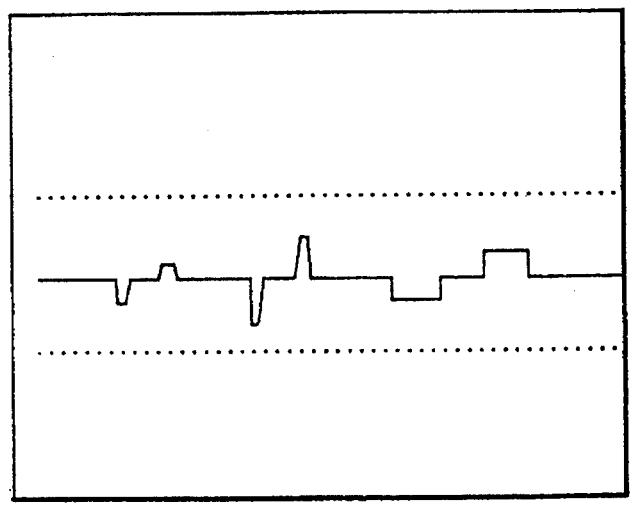
FIG. 13 is a frame showing a difference image for the one dimensional array.
Figure 14:
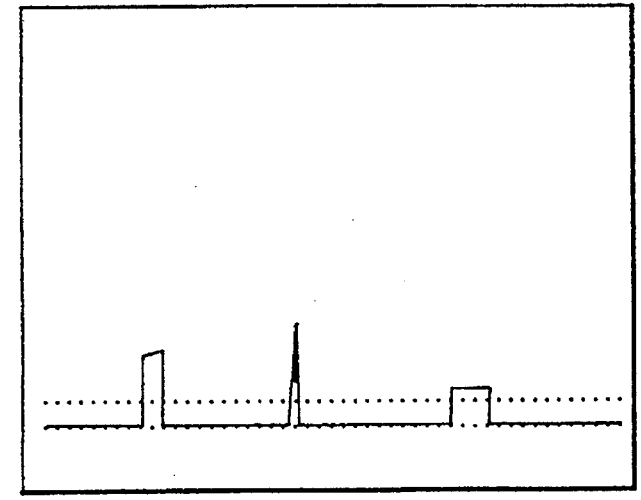
FIG. 14 is a frame showing the vertically projected difference image after convolution.

In the sixth operation 34 (Filter And Check Limit), a two dimensional convolution kernel is selected which enhances only the complimentary pairs with the same offset as that between the images which are subtracted. Residuals with the knurling period and other noise will be suppressed. To increase execution speed with less electronic memory requirements (with some loss of sensitivity), a Density Projection 36 operation may be added to the algorithm illustrated in FIG. 2, either before (FIG. 11) as shown in FIG. 12 or after (FIG. 15) the Difference With Offset operation 30. The Density Projection operation reduces the image to a one dimensional array (FIG. 13) by vertical projection (summing along the pixel columns or by horizontal projection (summing along pixel rows where the remapped image is essentially vertical), performing Density Projection above the Difference With Offset operation, which achieves maximum speed with a potentially greater cost in sensitivity. This step is not fundamentally necessary but it does drastically reduce the number of computations required for the next step at the cost of sensitivity to defects. The decision to include this reduction must be made considering the conflicting requirements of speed and sensitivity. Given sufficient computational capability for the allotted inspection time, this step could be omitted entirely.

Density Projection 34 serves to enhance the signals (FIG. 12) caused by the defects and suppress other signals such as noise and residual artifacts from the subtraction process. The ratio relating the knurling pitch and the pixel pitch may be irrational. This condition may not permit alignment between the knurling of the two images (the remapped image and the offset remapped images) such that the two completely cancel in the difference image. Also, there might exist inconsistencies in the knurling pattern which give rise to residual structure in the difference image. In both these cases, however, the residuals have a period equal to the pixel pitch whereas the signal, due to defects, has a period equal to image offset. The filtered image will appear as a topographical 3-D presentation and the height of the defect (Intensity) will be subject to a selected threshold. If the data has been reduced to a one dimensional array as in operation 5, then a one dimensional convolution kernel will suffice. If the data has not been reduced, then a two dimensional kernel will be necessary.

I claim:

1. A machine for inspecting the annular knurled area on the bottom of a glass or plastic container for defects comprising means for supporting a container at an inspection location so that light can pass through the bottom of the container to the opening of the container, a diffuse light source for illuminating the container from below, an electronic area array camera having a lens for projecting an image of the container bottom viewed through the opening of the container on the array, means for digitizing the camera image signal so that it may be represented in digital memory, means for analyzing said digitized image including means for remapping the annular knurled area to define at least one remapped, straight line area means for copying said remapped, straight line area with a lateral offset, means for subtracting said laterally offset copy of said remapped, straight line area from said remapped, straight line area to define a difference image in which the knurling disappears, means for convolving the difference image to emphasize defects, and means for defining a threshold on said convolved difference image to indicate the presence of defects.

2. A machine for inspecting the annular knurled area on the bottom of a glass or plastic container according to claim 1, wherein said means for remapping the annular knurled area comprises means for copying the remapped area with an offset substantially equal to a whole number of knurling periods.

3. A machine for inspecting the annular knurled area on the bottom of a glass or plastic container according to claim 2, wherein said remapping means remaps the annular area into a rectangular area.

4. A machine for inspecting the annular knurled area on the bottom of a glass or plastic container for defects comprising means for supporting a container at an inspection location so that light can pass through the bottom of the container to the opening of the container, a diffuse light source for illuminating the container from below, an electronic area array camera having a lens for projecting an image of the container bottom viewed through the opening of the container on the array, means for digitizing the camera image signal for the annular knurled area so that it may be represented in digital memory, means for analyzing said digitized annular knurled area including means for subtracting selectively offset pixels of said digitized annular knurled area to define a difference image in which the knurling disappears, means for convolving the difference image to emphasize defects, and means for defining a threshold on said convolved difference image to indicate the presence of defects.

* * * * *